US008933298B2

(12) United States Patent
Jahn et al.

(10) Patent No.: US 8,933,298 B2
(45) Date of Patent: Jan. 13, 2015

(54) MUTATED EIF4E SEQUENCES FROM POTATO WHICH IMPART RESISTANCE TO POTATO VIRUS Y

(75) Inventors: Margaret Jahn, Lansing, NY (US); Jason Cavatorta, Davis, CA (US); Inhwa Yeam, Seoul (KR)

(73) Assignee: Cornell University, Ithaca, NY (US)

( * ) Notice: Subject to any disclaimer, the term of this patent is extended or adjusted under 35 U.S.C. 154(b) by 675 days.

(21) Appl. No.: 13/125,429

(22) PCT Filed: Oct. 22, 2009

(86) PCT No.: PCT/US2009/061675
§ 371 (c)(1), (2), (4) Date: Aug. 4, 2011

(87) PCT Pub. No.: WO2010/048398
PCT Pub. Date: Apr. 29, 2010

(65) Prior Publication Data

US 2011/0289633 A1 Nov. 24, 2011

Related U.S. Application Data

(60) Provisional application No. 61/107,525, filed on Oct. 22, 2008, provisional application No. 61/113,919, filed on Nov. 12, 2008.

(51) Int. Cl.

| | |
|---|---|
| ***C07H 21/04*** | (2006.01) |
| ***C12N 15/00*** | (2006.01) |
| ***C12N 15/74*** | (2006.01) |
| ***C12N 15/82*** | (2006.01) |
| ***A01H 5/00*** | (2006.01) |
| ***A01H 5/10*** | (2006.01) |
| ***C07K 14/415*** | (2006.01) |

(52) U.S. Cl.
CPC .......... *C07K 14/415* (2013.01); *C12N 15/8283* (2013.01)
USPC ........ 800/279; 800/298; 800/301; 800/317.2; 800/305; 800/306; 800/320.1; 800/320.2; 800/320.3; 800/307; 800/309; 435/320.1; 536/23.6; 424/93.2; 424/93.21

(58) Field of Classification Search
None
See application file for complete search history.

(56) References Cited

U.S. PATENT DOCUMENTS

| | | | |
|---|---|---|---|
| 7,772,462 | B2 | 8/2010 | Jahn et al. |
| 2002/0132346 | A1 | 9/2002 | Cibelli |
| 2003/0106101 | A1 | 6/2003 | Thompson et al. |
| 2005/0108791 | A1 | 5/2005 | Edgerton |
| 2005/0255455 | A1 | 11/2005 | Caranta et al. |
| 2006/0294618 | A1 | 12/2006 | Jahn et al. |

FOREIGN PATENT DOCUMENTS

| | | | |
|---|---|---|---|
| FR | 2 835 698 | A1 | 8/2003 |
| FR | 2 835 849 | A1 | 8/2003 |
| WO | 01/40490 | A2 | 6/2001 |
| WO | 03/066900 | A2 | 8/2003 |
| WO | 2004/057941 | A2 | 7/2004 |

OTHER PUBLICATIONS

McDonald et al. Host range, symptomology, and serology of isolates of *Potato virus y* (PVY) that share properties with both the PVY N and PVY O strain groups. 1996. American Potato Journal. 73:309-315.*

Yeam et al. Functional dissection of naturally occurring amino acid substitutions in eIF4E that confers recessive polyvirus resistance in plants. 2007. The Plant Cell. 19(9):2913-2928).*

Bruun-Rasmussen et al., "The Same Allele of Translation Initiation Factor 4E Mediates Resistance Against Two *Potyvirus* spp. in *Pisum sativum*," Mol. Plant Microbe Interact. 20(9)1075-1082 (2007).

Cavatorta et al., "Molecular Evolutionary Analysis of Resistance Gene eIF4E and Creation of Novel Resistance Alleles in Potato," Phytopathology 98(6):S9; S33 (2008) (Abstract).

Charron et al., "Natural Variation and Functional Analyses Provide Evidence for Co-Evolution Between Plant eIF4E and Potyviral VPg," Plant J. 54:56-68 (2008).

Gao et al., "The *Potyvirus* Recessive Resistance Gene, sbm1, Identifies a Novel Role for Translation Initiation Factor eIF4E in Cell-to-Cell Trafficking," Plant J. 40:376-385 (2004).

German-Retana et al., "Mutational Analysis of Plant Cap-Binding Protein eIF4E Reveals Key Amino Acids Involved in Biochemical Functions and *Potyvirus* Infection," J. Virol. 82(15):7601-7612 (2008).

Marandel et al., "Quantitative Resistance to Plum pox Virus in *Prunus davidiana* P1908 Linked to Components of the Eukaryotic Translation Initiation Complex," Plant Pathol. 58:425-435 (2009).

Ruffel et al., "Simultaneous Mutations in Translation Initiation Factors eIF4E and eIF(iso)4E are Required to Prevent Pepper Veinal Mottle Virus Infection of Pepper," J. Gen. Virol. 87:2089-2098 (2006).

Sicard et al., "Flanking the Major Plum pox Virus Resistance Locus in Apricot With Co-Dominant Markers (SSRs) Derived From Candidate Resistance Genes," Tree Genetics & Genomes 4:359-365 (2008).

Yeam et al., "Allele-Specific CAPS Markers Based on Point Mutations in Resistance Alleles at the pvr1 Locus Encoding eIF4E in *Capsicum*," Theor. Appl. Genet. 112(1):178-186 (2005).

(Continued)

*Primary Examiner* — Cathy Kingdon Worley
*Assistant Examiner* — Jeffrey Bolland
(74) *Attorney, Agent, or Firm* — LeClairRyan, a Professional Corporation

(57) ABSTRACT

The present invention relates to a nucleic acid molecule encoding a mutant form of wild-type translation initiation factor eIF4E, which has an amino acid sequence of SEQ ID NO: 1, wherein the mutant form imparts resistance to Potato virus Y and has a mutation with respect to the wild-type amino acid sequence of SEQ ID NO: 1 selected from the group consisting of: (1) any one or more of I70N, I70E, L82R, and D112N and (2) any one or more of L48F, S68K, A77D, and M109I. Nucleic acid constructs, expression vectors, cells, plants, and plant seeds containing the nucleic acid molecule of the present invention, are also disclosed, as are methods of imparting resistance to Potato virus Y to plants.

20 Claims, 8 Drawing Sheets

(56) References Cited

OTHER PUBLICATIONS

Yeam et al., "Functional Dissection of Naturally Occurring Amino Acid Substitutions in eIF4E That Confers Recessive *Potyvirus* Resistance in Plants," Plant Cell 19:2913-2928 (2007).
PCT International Search Report and Written Opinion for PCT/US2009/061675, mailed Apr. 5, 2010.
Ruffel et al., "The Recessive *Potyvirus* Resistance Gene pot-1 is the Tomato Orthologue of the Pepper pvr2-eIF4E Gene," Mol. Gen. Genomics 274:346-353 (2005).
GenBank Accession No. FN666435, Mar. 3, 2010.
Duprat et al., "The *Arabidopsis* Eukaryotic Initiation Factor (iso)4E is Dispensable for Plant Growth but Required for Susceptibility to Potyviruses," Plant J. 32:927-34 (2002).
Gallie, "Cap-independent Translation Conferred by the 5' Leader of Tobacco Etch Virus is Eukaryotic Initiation Factor 4G Dependent," J. Virol. 75(24):12141-12152 (2001).
Lellis et al., "Loss-of-Susceptibility Mutants of *Arabidopsis thaliana* Reveal an Essential Role for eIF(iso)4E During *Potyvirus* Infection," Curr. Biol. 12:1046-1051 (2002).
Léonard et al., "Complex Formation Between *Potyvirus* VPg and Translation Eukaryotic Initiation Factor 4E Correlates with Virus Infectivity," J. Virol. 74(17):7730-7737 (2000).
Nicaise et al., "The Eukaryotic Translation Initiation Factor 4E Controls Lettuce Susceptibility to the *Potyvirus* Lettuce mosaic virus," Plant Physiol. 132:1272-1282 (2003).
Ruffel et al., "A Natural Recessive Resistance Gene Against *Potato virus Y* in Pepper Corresponds to the Eukaryotic Initiation Factor 4E (eIF4E)," Plant J. 32:1067-1075 (2002).
Schaad et al., "Strain-specific Interaction of the Tobacco Etch Virus Nla Protein with the Translation Initiation Factor eIF4E in the Yeast Two-Hybrid System," Virol. 273:300-306 (2000).
Wittmann et al., "Interaction of the Viral Protein Genome Linked of Turnip Mosaic *Potyvirus* with the Translational Eukaryotic Initiation Factor (iso) 4E of *Arabidopsis thaliana* Using the Yeast Two-hybrid System," Virol. 234:84-92 (1997).
Yoshii et al., "The *Arabidopsis cucumovirus* Multiplication 1 and 2 Loci Encode Translation Initiation Factors 4E and 4G," J. Virol. 78(12):6102-6111 (2004).
Yamanaka et al., "TOM1, an *Arabidopsis* Gene Required for Efficient Multiplication of a *Tobamovirus*, Encodes a Putative Transmembrane Protein," Proc. Nat'l Acad. Sci. USA 97(18):10107-10112 (2000).
GenBank Accession No. AAM82190, Mar. 16, 2005.
GenBank Accession No. AAR23916, Apr. 21, 2005.
GenBank Accession No. AAR23917, Apr. 21, 2005.
GenBank Accession No. AAR23918, Apr. 21, 2005.
GenBank Accession No. AAR23919, Apr. 21, 2005.
GenBank Accession No. AAR23920, Apr. 21, 2005.
GenBank Accession No. AY122052, Mar. 16, 2005.
GenBank Accession No. AY485129, Apr. 21, 2005.
GenBank Accession No. AY485130, Apr. 21, 2005.
GenBank Accession No. AY485131, Apr. 21, 2005.
Falcon-Perez et al., "Functional Domain Analysis of the Yeast ABC Transporter Ycf1p by Site-Directed Mutagenesis," J. Biol. Chem. 274(33):23584-23590 (1999).
Guo et al., "Protein Tolerance to Random Amino Acid Change," Proc. Nat'l. Acad. Sci. USA 101(25):9205-9210 (2004).
Hill and Preiss, "Functional Analysis of Conserved Histidines in ADP-Glucose Pyrophosphorylase from *Escherichia coli*," Biochem, Biophys. Res. Commun. 244(2):573-577 (1998).
Lazar et al., "Transforming Growth Factor [Alpha]: Mutation of Aspartic Acid 47 and Leucine 48 Results in Different Biological Activities," Mol. Cell. Biol. 8(3):1247-1252 (1988).

* cited by examiner

SEQUENCE LISTING

```
<160> NUMBER OF SEQ ID NOS: 13

<210> SEQ ID NO 1
<211> LENGTH: 231
<212> TYPE: PRT
<213> ORGANISM: Solanum tuberosum

<400> SEQUENCE: 1

Met Ala Thr Ala Glu Met Glu Arg Thr Thr Ser Phe Asp Ala Ala Glu
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Thr Ala Ser Tyr Leu
```

-continued

```
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Tyr Val Glu Asp Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Asn Phe Leu Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ser Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Ser
    210                 215                 220

Ala Lys Asn Arg Tyr Thr Val
225                 230
```

<210> SEQ ID NO 2
<211> LENGTH: 696
<212> TYPE: DNA
<213> ORGANISM: Solanum tuberosum

<400> SEQUENCE: 2

```
atggcaacag ctgaaatgga gagaacgacg tcgtttgatg cagctgagaa gttgaaggcc      60

gccgatgcag gaggaggaga ggtagacgat gaacttgaag aaggtgaaat tgttgaagaa     120

tcaaatgata cggcgtcgta tttagggaaa gaaatcacag tgaaacatcc attggagcat     180

tcatggactt tttggtttga tagccctatt gctaaatctc gacaaactgc ttggggaagc     240

tcacttcgaa atgtctacac tttctccact gttgaagatt tttggggtgc ttacaataat     300

atccatcacc caagcaagtt ggttatggga gcagactttc attgttttaa gcataaaatt     360

gagccaaagt gggaagatcc tgtatgtgcc aatggaggga cgtggaaaat gaatttttg      420

aagggtaaat ctgataccag ctggctatat acgctgctgg caatgattgg acatcaattc     480

gatcacggag atgaaatttg tggagcagtc gttagtgtcc ggtctaaggg agaaaaaata     540

gctttgtgga ccaagaatgc tgcaaatgaa acagctcagg ttagcattgg taagcaatgg     600

aagcagtttc tagattacag cgattcggtt ggcttcatat ttcacgatga tgcaaagagg     660

ctcgacagaa gtgccaagaa tcgttacacc gtatag                               696
```

<210> SEQ ID NO 3
<211> LENGTH: 696
<212> TYPE: DNA
<213> ORGANISM: Solanum tuberosum

<400> SEQUENCE: 3

```
atggcaacag ctgaaatgga gagaacgacg tcgtttgatg cagctgagaa gttgaaggcc      60
```

gccgatgcag gaggaggaga ggtagacgat gaacttgaag aaggtgaaat tgttgaagaa 120
tcaaatgata cggcgtcgta tttggggaaa gaaatcacag tgaagcatcc attggagcat 180
tcatggactt tttggtttga tagccctatt gctaaatctc gacaaactgc ttggggaagc 240
tcacttcgaa atgtctacac tttctccact gttgaagagt tttggggtgc ttacaataat 300
atccatcacc caagcaagtt ggttatggga gcagactttc attgttttaa gcataaaatt 360
gagccaaagt gggaagatcc tgtatgtgcc aatggaggga cgtggaaaat gagtttttg 420 aagggtaaat ctgataccag ctggctatat acgctgctgg ctatgattgg acatcaattt 480
gatcatggag atgaaatttg tggagcagtc gttagtgtcc ggtctaaggg agaaaaaata 540
gctttgtgga ccaagaatgc tgcaaatgaa acagctcagg ttagcattgg taagcaatgg 600
aagcagtttc tagatcatag cgattcggtt ggcttcatat ttcatgacga tgcaaagagg 660
ctcgacagaa gtgccaagaa tcgttacacc gtatag 696

<210> SEQ ID NO 4
<211> LENGTH: 696
<212> TYPE: DNA
<213> ORGANISM: Solanum tuberosum

<400> SEQUENCE: 4
atggcaacag ctgaaatgga gagaacgacg tcgtttgatg cagctgagaa gttgaaggcc 60
gccgatgcag gaggaggaga ggtagacgat gaacttgaag aaggtgaaat tgttgaagaa 120
tcaaatgata cggcgtcgta tttagggaaa gaaatcacag tgaaacatcc attggagcat 180
tcatggactt tttggtttga tagccctatt gctaaatctc gacaaactgc ttggggaagc 240
tcacttcgaa atgtctacac tttctccact gttgaagatt tttggggtgc ttacaataat 300
atccatcacc caagcaagtt ggttatggga gcagactttc attgttttaa gcataaaatt 360
gagccaaagt gggaagatcc tgtatgtgcc aatggaggga cgtggaaaat gagtttttg 420 aagggtaaat ctgataccag ctggctatat acgctgctgg ctatgattgg acatcaattt 480
gatcatggag atgaaatttg tggagcagtc gttagtgtcc ggtctaaggg agaaaaaata 540
gctttgtgga ccaagaatgc tgcaaatgaa acagctcagg ttagcattgg taagcaatgg 600
aagcagtttc tagatcatag cgattcggtt ggcttcatat ttcatgacga tgcaaagagg 660
ctcgacagaa gtgccaagaa tcgttacacc gtatag 696

<210> SEQ ID NO 5
<211> LENGTH: 231
<212> TYPE: PRT
<213> ORGANISM: Solanum lycopersicum

<400> SEQUENCE: 5

Met Ala Ala Ala Glu Met Glu Arg Thr Met Ser Phe Asp Ala Ala Glu
1 5 10 15

Lys Leu Lys Ala Ala Asp Gly Gly Gly Gly Glu Val Asp Asp Glu Leu
20 25 30

Glu Glu Gly Glu Ile Val Glu Glu Ser Asn Asp Thr Ala Ser Tyr Leu
35 40 45

Gly Lys Glu Ile Thr Val Lys His Pro Leu Glu His Ser Trp Thr Phe
50 55 60

Trp Phe Asp Asn Pro Thr Thr Lys Ser Arg Gln Thr Ala Trp Gly Ser
65 70 75 80

Ser Leu Arg Asn Val Tyr Thr Phe Ser Thr Val Glu Asp Phe Trp Gly

-continued

```
                85                  90                  95

Ala Tyr Asn Asn Ile His His Pro Ser Lys Leu Ile Met Gly Ala Asn
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Ser Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 6
<211> LENGTH: 228
<212> TYPE: PRT
<213> ORGANISM: Capsicum annuum

<400> SEQUENCE: 6

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220
```

```
Arg Tyr Thr Val
225


<210> SEQ ID NO 7
<211> LENGTH: 28
<212> TYPE: DNA
<213> ORGANISM: Artificial
<220> FEATURE:
<223> OTHER INFORMATION: Primer

<400> SEQUENCE: 7

tcccccggga tggcaacagc tgaaatgg                                        28


<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8

tccgagctcc tatacggtgt aacg                                            24


<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9

ccgaattcat ggcaacagct ga                                              22


<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10

tccctcgagc tatacggtgt aacg                                            24


<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11

tccgaattca tgaaaaataa atccaaaag                                       29


<210> SEQ ID NO 12
<211> LENGTH: 33
<212> TYPE: DNA
<213> ORGANISM: Artificial
<220> FEATURE:
<223> OTHER INFORMATION: Primer

<400> SEQUENCE: 12

tccctcgagc taatgctcca cttcctgttt tgg                                  33


<210> SEQ ID NO 13
<211> LENGTH: 24
<212> TYPE: DNA
```

-continued

```
<213> ORGANISM: Artificial
<220> FEATURE:
<223> OTHER INFORMATION: Primer

<400> SEQUENCE: 13

gctcctacaa atgccatcat tgcg                                              24
```

MUTATED EIF4E SEQUENCES FROM POTATO WHICH IMPART RESISTANCE TO POTATO VIRUS Y

This application claims the benefit of U.S. Provisional Patent Application Ser. No. 61/107,525, filed Oct. 22, 2008, and U.S. Provisional Patent Application Ser. No. 61/113,919, filed Nov. 12, 2008.

This invention was made with government support under grant number 0218166 by the National Science Foundation. The government has certain rights in this invention.

FIELD OF THE INVENTION

The present invention is directed to mutated eIF4E sequences from potato which are useful in imparting virus resistance.

BACKGROUND OF THE INVENTION

The Potyviridae family is characterized by a positive sense single stranded RNA genome and a flexuous elongated particle measuring 650 to 900 nm in length. Potyviruses are found worldwide and can cause substantial disruption to host plant growth and development either from single infection or synergistically during coinfection with other viruses (Hull R, *Mathews' Plant Virology*, Academic Press (2001); Shukla et al., *The Potyviridae*. CAB International, Wallingford (1994). To address the challenges that potyviruses have posed to pepper and tomato production, plant breeders have utilized a number of recessively inherited resistance sources.

In pepper, resistance allele pvr1 was discovered in two accessions of *Capsicum chinense* and is effective against particular strains of Potato virus Y (PVY), Tobacco etch virus (TEV), and Pepper mottle virus (PepMoV). Allele pvr1$^{1}$ was discovered in two cultivated varieties of *Capsicum annuum* and is known to confer resistance against only a few strains of PVY. Resistance allele pvr1$^{2}$ was discovered in two accessions of *Capsicum annuum*. It provides resistance against a broad range of PVY and TEV strains. Natural virus resistance within *Capsicum* has proven somewhat difficult to breed with due to its recessive inheritance but continues to be highly durable and effective even after decades of commercial use. In tomato, the virus resistance allele pot-1 was identified in *Solanum habrochaites* (formerly *Lycopersicon hirsutum*) (Parrella et al., "Recessive Resistance Genes Against Potyviruses are Localized in Colinear Genomic Regions of the Tomato (*Lycopersicon* spp.) and Pepper (*Capsicum* spp.) Genomes," *Theor Appl Genet.* 105:855-861 (2002)). This recessive resistance gene has been shown to provide resistance against both Tobacco etch virus (TEV) and Potato virus Y (PVY).

The pvr1 and pot-1 loci of pepper and tomato, respectively, have been shown to encode orthologous copies of the eukaryotic translation initiation factor 4E (eIF4E), a protein involved in binding to the 5' cap of messenger RNA and aiding in recruitment to the host ribosomal complex (Gingras et al., "eIF4 Initiation Factors: Effectors of mRNA Recruitment to Ribosomes and Regulators of Translation," *Annu Rev Biochem* 68:913-63 (1999); Kang et al., "The pvr1 Locus in *Capsicum* Encodes a Translation Initiation Factor eIF4E that Interacts with Tobacco Etch Virus VPg," *Plant J* 42:392-405 (2005); Ruffel et al., "A Natural Recessive Resistance Gene Against Potato Virus Y in Pepper Corresponds to the Eukaryotic Initiation Factor 4E (eIF4E)," *Plant J* 32:1067-75 (2002); Ruffel et al., "The Recessive Potyvirus Resistance Gene Pot-1 is the Tomato Orthologue of the Pepper pvr2-eIF4E Gene," *Mol Genet Genomics* 274:346-53 (2005)). During viral infection, eIF4E has been shown to bind to the viral genome-linked protein (VPg) (Leonard et al., "Complex Formation Between Potyvirus VPg and Translation Eukaryotic Initiation Factor 4E Correlates with Virus Infectivity," *J Virol* 74:7730-7 (2000); Schaad et al., "Strain-Specific Interaction of the Tobacco Etch Virus NIa Protein with the Translation Initiation Factor eIF4E in the Yeast Two-hybrid System," *Virology* 273:300-6 (2000)). eIF4E binding with VPg is thought to facilitate translation of the virus genome, replication of the virus genome, and/or cell-to-cell movement of the virus (Gao et al., "The Potyvirus Recessive Resistance Gene, sbm1, Identifies a Novel Role for Translation Initiation Factor eIF4E in Cell-To-Cell Trafficking," *The Plant Journal* 40:376-385 (2004); Kang et al., "The pvr1 Locus in *Capsicum* Encodes a Translation Initiation Factor eIF4E that Interacts with Tobacco Etch Virus VPg," *Plant J* 42:392-405 (2005); Robaglia et al., "Translation Initiation Factors: A Weak Link in Plant RNA Virus Infection," *Trends Plant Sci* 11:40-5 (2006)). Resistant alleles of eIF4E differ from wild-type sequences by only a few amino acid changes. Resistant versions of eIF4E disrupt the interaction with VPg, which often leads to strain-specific virus resistance.

In addition to pepper and tomato, recessive resistance alleles at the eIF4E locus have been identified in lettuce (Nicaise et al., "The Eukaryotic Translation Initiation Factor 4E Controls Lettuce Susceptibility to the Potyvirus Lettuce Mosaic Virus," *Plant Physiol* 132:1272-82 (2003)), barley (Stein et al., "The Eukaryotic Translation Initiation Factor 4E Confers Multiallelic Recessive Bymovirus Resistance in *Hordeum Vulgare* (L.)," *Plant J* 42:912-22 (2005)), pea (Gao et al., "The Potyvirus Recessive Resistance Gene, sbm1, Identifies a Novel Role for Translation Initiation Factor eIF4E in Cell-To-Cell Trafficking," *The Plant Journal* 40:376-385 (2004)), and melon (Nieto et al., "An eIF4E Allele Confers Resistance to an Uncapped and Non-Polyadenylated RNA Virus in Melon," *Plant J* 48:452-62 (2006)). However, despite the fact that potyviruses result in significant yield losses in cultivated potato, only dominant potyvirus resistance has been identified in potato to date (Solomon-Blackburn et al., "A Review of Host Major-Gene Resistance to Potato Viruses X, Y, A and V in Potato: Genes, Genetics and Mapped Locations," *Heredity* 86:8-16 (2001)).

The present invention is directed to overcoming these and other deficiencies in the art.

SUMMARY OF THE INVENTION

The present invention relates to a nucleic acid molecule encoding a mutant form of wild-type translation initiation factor eIF4E, which has an amino acid sequence of SEQ ID NO: 1, wherein the mutant form imparts virus resistance to potato and has a mutation with respect to the wild-type amino acid sequence of SEQ ID NO: 1 selected from the group consisting of: (1) any one or more of I70N, I70E, L82R, and D112N and (2) any one or more of L48F, S68K, A77D, and M109I.

The present invention further relates to a nucleic acid construct comprising a promoter and termination sequence, a recombinant expression vector, and a host cell containing the nucleic acid molecule, as well as a transgenic plant and a transgenic plant seed transformed with the nucleic acid molecule.

The present invention also relates to a method of imparting virus resistance to plants. This method involves providing a transgenic plant or a transgenic plant seed comprising the nucleic acid molecule encoding a mutant form of wild-type translation initiation factor eIF4E, which has an amino acid sequence of SEQ ID NO: 1 and growing the transgenic plant or a plant produced from the transgenic plant seed under conditions effective to impart virus resistance to the plant.

The present invention further relates to transgenic plants produced by this method, as well as component parts, seeds, and fruits of the transgenic plant.

The present invention also relates to a method of imparting virus resistance to plants which involves providing a plant cell comprising nucleic acid molecules encoding the mutant form of wild-type translation initiation factor eIF4E, which has the amino acid sequence of SEQ ID NO: 1. The method further involves regenerating plants from the plant cells, such that the regenerated plants are virus resistant.

Previous studies have shown that transgenic expression of resistance alleles from pepper confers virus-resistance in tomato (Kang B et al., "Ectopic Expression of a Recessive Resistance Gene Generates Dominant Potyvirus Resistance in Plants," *Plant Biotechnol J* (2007), which is hereby incorporated by reference in its entirety). The present invention describes the sequencing of wildtype susceptible potato eIF4E and the generation of novel potato eIF4E alleles mimicking virus resistance alleles in other species. These novel alleles disrupt the interaction between potato eIF4E and viral VPg. The novel potato eIF4E alleles are expressed transgenically in potato, and virus resistant potato transformants are obtained. This is a positive development not only because virus resistant plants have been developed but also because a gene from within the potato genome was utilized to do so. Such 'intragenic' expression of genes, where the donor and recipient of a transgene are within sexually reproductive barriers, is appealing, because it may address consumer concerns regarding adoption of genetically modified potatoes (Nielsen K., "Transgenic Organisms—Time For Conceptual Diversification?," *Nat Biotechnol* 21:227-8 (2003), which is hereby incorporated by reference in its entirety).

BRIEF DESCRIPTION OF THE DRAWINGS

FIG. 3A shows the interaction (blue) or lack of interaction (white) observed between several versions of potato eIF4E and two strains of Potato virus Y (PYV) VPg: O and NTN. Controls consisted of wildtype potato eIF4E (positive control) and empty vector (negative control). FIG. 3B shows results from an immunoblot assay. Approximately equal amounts of protein were loaded for the assay. Protein was extracted from a liquid culture expressing PVY-NTN VPg and the eIF4E variant shown. FIG. 3C is a western blot using an anti-mouse hemagglutinin (HA) antibody. This figure shows that all of the eIF4E variants tested are expressed in yeast cells.

In FIG. 4B, lanes 1 through 23 are potentially transgenic plants, lane 24 is an untransformed plant, lane 25 is a water negative control, and lane 26 is a vector DNA positive control.

DETAILED DESCRIPTION OF THE INVENTION

Figure 1:
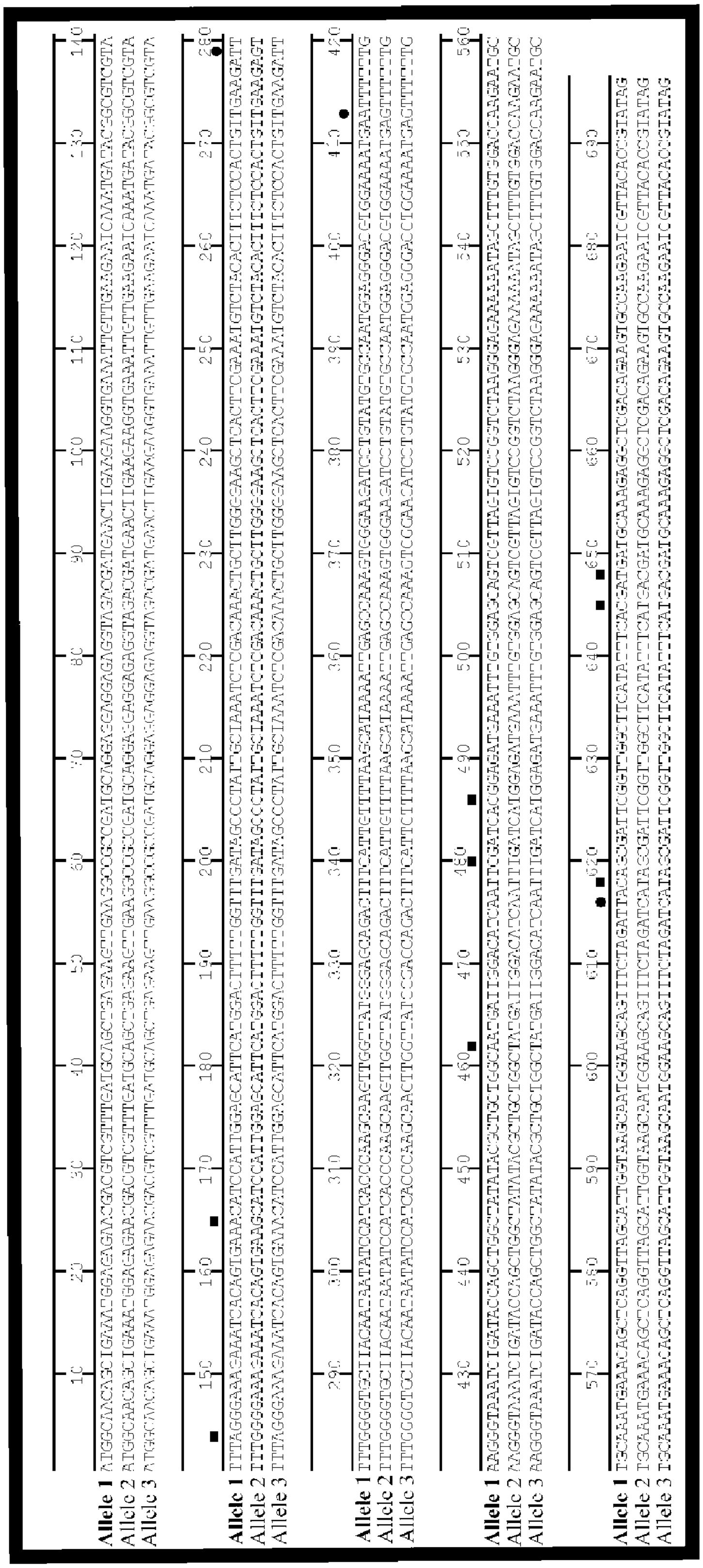
FIG. 1 is the nucleotide alignment of the three potato eIF4E alleles (allele 1 corresponds to nucleotide sequence of SEQ ID NO: 2, allele 2 corresponds to the nucleotide sequence of SEQ ID NO: 3, allele 3 corresponds to the nucleotide sequence of SEQ ID NO: 4) sequenced from cultivar 'Russet Burbank' clone 'Ida'. Solid squares identify nucleotides that have a synonymous polymorphism between alleles. Solid circles identify nucleotides that have a nonsynonymous polymorphism between alleles.

The present invention relates to a nucleic acid molecule encoding a mutant form of wild-type translation initiation factor eIF4E, which has an amino acid sequence of SEQ ID NO: 1, wherein the mutant form imparts virus resistance to potato and has a mutation with respect to the wild-type amino acid sequence of SEQ ID NO: 1 selected from the group consisting of: (1) any one or more of I70N, I70E, L82R, and D112N and (2) any one or more of L48F, S68K, A77D, and M109I.

SEQ ID NO:1, which is the amino acid sequence of wild-type eIF4E, is as follows:

```
  1 MATAEMERTT SFDAAEKLKA ADAGGGEVDD ELEEGEIVEE SNDTASYLGK
 51 EITVKHPLEH SWTFWFDSPI AKSRQTAWGS SLRNVYTFSY VEDFWGAYNN
101 IHHPSKLVMG ADFHCFKHKI EPKWEDPVCA NGGTWKMNFL KGKSDTSWLY
```

-continued

```
151 TLLAMIGHQF DHGDEICGAV VSVRSKGEKI ALWTKNAANE TAQVSIGKQW

201 KQFLDYSDSV GFIFHDDAKR LDRSAKNRYT V
```

The nucleotide sequence encoding the protein of SEQ ID NO: 1 is SEQ ID NO: 2 which reads as follows:

```
  1 ATGGCAACAG CTGAAATGGA GAGAACGACG TCGTTTGATG CAGCTGAGAA

 51 GTTGAAGGCC GCCGATGCAG GAGGAGGAGA GGTAGACGAT GAACTTGAAG

101 AAGGTGAAAT TGTTGAAGAA TCAAATGATA CGGCGTCGTA TTTAGGGAAA

151 GAAATCACAG TGAAACATCC ATTGGAGCAT TCATGGACTT TTTGGTTTGA

201 TAGCCCTATT GCTAAATCTC GACAAACTGC TTGGGGAAGC TCACTTCGAA

251 ATGTCTACAC TTTCTCCACT GTTGAAGATT TTTGGGGTGC TTACAATAAT

301 ATCCATCACC CAAGCAAGTT GGTTATGGGA GCAGACTTTC ATTGTTTTAA

351 GCATAAAATT GAGCCAAAGT GGGAAGATCC TGTATGTGCC AATGGAGGGA

401 CGTGGAAAAT GAATTTTTTG AAGGGTAAAT CTGATACCAG CTGGCTATAT

451 ACGCTGCTGG CAATGATTGG ACATCAATTC GATCACGGAG ATGAAATTTG

501 TGGAGCAGTC GTTAGTGTCC GGTCTAAGGG AGAAAAAATA GCTTTGTGGA

551 CCAAGAATGC TGCAAATGAA ACAGCTCAGG TTAGCATTGG TAAGCAATGG

601 AAGCAGTTTC TAGATTACAG CGATTCGGTT GGCTTCATAT TTCACGATGA

651 TGCAAAGAGG CTCGACAGAA GTGCCAAGAA TCGTTACACC GTATAG
```

The gene product of the eIF4E gene is part of the eIF4F complex (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety). In this complex, eIF4E provides a 5' cap-binding function during formation of translation initiation complexes in mRNAs of eukaryotes.

A suitable gene encoding the translation initiation factor eIF4E ("eIF4E gene") that can be targeted for the methods of the present invention can include, for example, any plant eIF4E gene naturally occurring in a virus-susceptible plant. In one embodiment, a suitable eIF4E gene can have a nucleotide sequence that is at least 70 percent similar to SEQ ID NO:1. In another embodiment, a suitable eIF4E gene can have a nucleotide sequence that is at least 90 percent similar to SEQ ID NO:1. In another embodiment, a suitable eIF4E gene can have a nucleotide sequence that is at least 95 percent similar to SEQ ID NO:1. In yet another embodiment, the eIF4E gene can have a nucleotide sequence that hybridizes to SEQ ID NO:1 under stringent hybridization conditions involving, for example, hybridization in a hybridization buffer containing, for example, 20 percent formamide in 0.9M saline/0.09M SSC buffer, at a temperature of about 42° C. Other suitable stringent conditions are described below.

For the purposes of defining the level of stringency, reference can conveniently be made to Sambrook et al., *Molecular Cloning: A Laboratory Manual,* 2nd Edition, Cold Spring Harbor, N.Y., Cold Spring Harbor Laboratory Press, (1989) which is hereby incorporated by reference in its entirety. An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at >45° C. for 2-3 hours. An example of high stringency conditions includes 0.1-1×SSC/0.1% w/v SDS at 60° C. for 1-3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

In one embodiment of the present invention, the nucleic acid molecule encoding a mutant form of wild-type translation initiation factor eIF4E, which has an amino acid sequence of SEQ ID NO: 1, can be a mutant form with any one or more mutations of I70N, I70E, L82R, and D112N with respect to SEQ ID NO: 1. In other embodiments, the mutant form can be with the mutations of I70E, L82R, and D112N with respect to SEQ ID NO: 1 or with the mutations of I70N, L82R, and D112N with respect to SEQ ID NO: 1.

In another embodiment of the present invention, the nucleic acid molecule encoding a mutant form of wild-type translation initiation factor eIF4E, which has an amino acid sequence of SEQ ID NO: 1, can be a mutant form with any one or more mutations of L48F, S68K, A77D, and M109I with respect to SEQ ID NO: 1.

The present invention also relates to a method of imparting virus resistance to plants. This method involves providing a transgenic plant or a transgenic plant seed comprising the nucleic acid molecule encoding a mutant form of wild-type translation initiation factor eIF4E, which has an amino acid sequence of SEQ ID NO: 1 and growing the transgenic plant or a plant produced from the transgenic plant seed under conditions effective to impart virus resistance to the plant. The present invention further relates to transgenic plants produced by this method, as well as component parts, seeds, and fruits of the transgenic plant.

The present invention also relates to a method of imparting virus resistance to plants which involves providing a plant cell comprising nucleic acid molecules encoding the mutant form of wild-type translation initiation factor eIF4E, which has the amino acid sequence of SEQ ID NO: 1. The method further involves regenerating plants from the plant cells, such that the regenerated plants are virus resistant.

The present invention also relates to a method of making a mutant translation initiation factor eIF4E. This method involves growing a host cell containing an isolated nucleic acid molecule encoding a mutant translation initiation factor eIF4E of the present invention under conditions whereby the host cell expresses the mutant translation initiation factor eIF4E. The mutant translation initiation factor eIF4E is then isolated. Further detail regarding this method is provided herein, infra.

The present invention also relates to an isolated mutant translation initiation factor eIF4E encoded by the corresponding nucleic acid molecule of the present invention (described, supra). The isolated mutant translation initiation factor eIF4E can be recombinant. The isolated mutant translation initiation factor eIF4E can also be in pure or non-pure form. A purified protein or polypeptide of the mutant translation initiation factor eIF4E of the present invention can be obtained by several methods. The purified protein or polypeptide of the mutant translation initiation factor eIF4E of the present invention is preferably produced in pure form (preferably at least about 80%, more preferably 90% pure) by conventional techniques well known in the art. Typically, the purified protein or polypeptide of the mutant translation initiation factor eIF4E of the present invention is secreted into the growth medium of recombinant host cells. Alternatively, the purified protein or polypeptide of the mutant translation initiation factor eIF4E of the present invention is produced but not secreted into growth medium. In such cases, to isolate the protein or polypeptide of the mutant translation initiation factor eIF4E, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the protein or polypeptide of the mutant translation initiation factor eIF4E of the present invention is subjected to gel filtration in an appropriately sized dextran or polyacrylamide column to separate the proteins. If necessary, the protein fraction (containing the mutant translation initiation factor eIF4E of the present invention) can be further purified by high performance liquid chromatography ("HPLC").

Another embodiment of the method of imparting virus resistance to plants involves providing a genetic construct containing the nucleic acid molecule of the present invention. The genetic construct is then used to transform a plant cell. In another embodiment, this method further involves propagating plants from the transformed plant cell. A suitable genetic construct for use in this method can further include a plant promoter and a terminator, where the plant promoter and the terminator are operatively coupled to the nucleic acid molecule. In one embodiment, the genetic construct is in an expression vector. As described in more detail, infra, transformation can be carried out by, without limitation, *Agrobacterium*-mediated transformation, biolistic transformation, and/or electroporation. Further, suitable techniques for the above aspects of the present invention's method of imparting virus resistance to plants are described in more detail, infra. This can involve incorporating the nucleic acid molecules of the present invention into host cells using conventional recombinant DNA technology. Generally, this involves inserting the nucleic acid molecule into an expression system, to which the nucleic acid molecule is heterologous (i.e., not normally present). The heterologous nucleic acid molecule is inserted into the expression system which includes the necessary elements for the transcription and translation of the inserted protein coding sequences. In one embodiment, the nucleic acid construct of the present invention contains the nucleic acid molecule of the present invention operatively connected to a promoter and termination sequence. The nucleic acid molecule is in proper sense orientation relative to the promoter. The present invention further relates to an expression system containing the genetic construct and a host cell transformed with the genetic construct. In one embodiment, the nucleic acid molecule is in proper sense orientation. In another particular embodiment, the host cell can be, without limitation, a plant cell or a bacterial cell. Further detail regarding the genetic construct, expression system, and host cells of the present invention are described herein, infra.

The nucleic acid molecules of the present invention can be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* 2nd Edition, Cold Spring Harbor, N.Y., Cold Spring Harbor Laboratory Press (1989); and Ausubel et al., *Current Protocols in Molecular Biology*, John Wiley & Sons, New York, N.Y., (1989) which are hereby incorporated by reference in their entirety.

In preparing a vector for expression, the various DNA sequences can normally be inserted or substituted into a bacterial plasmid. Any convenient plasmid can be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi or Ti-DNA, for "tumor inducing plasmid," contains the vir genes necessary for movement of the T-DNA into the plant.

The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch et al., "Complete Sequence of the Binary Vector Bin19," *Plant Mol. Biol.* 27:405-409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase ("NOS") gene promoter, from *Agrobacterium tumefaciens* (U.S. Pat. No. 5,034,322 issued to Rogers et al., which is hereby incorporated by reference in its entirety), the cauliflower mosaic virus ("CaMV") 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter ("ubi"), which is the promoter of a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11: 605-612 (1997), and McNellis et al., "Glucocorticoid-Inducible Expression of a Bacterial Avirulence Gene in Transgenic *Arabidopsis* Induces Hypersensitive Cell Death, *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference in its entirety). In one embodiment of the present invention, a heterologous promoter is linked to the nucleic acid of the construct, where "heterologous promoter" is defined as a promoter to which the nucleic acid of the construct is not linked in nature.

The nucleic acid construct also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA,* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would suffice for proper expression of the coding sequence of the nucleic acid of the present invention.

The vector of choice, suitable promoter, and an appropriate 3' regulatory region can be ligated together to produce the nucleic acid construct which contains the nucleic acid molecule of the present invention, or suitable fragments thereof, using well known molecular cloning techniques as described in Sambrook et al., *Molecular Cloning: A Laboratory Manual,* 2nd Edition, Cold Spring Harbor, N.Y., Cold Spring Harbor Laboratory Press (1989); Ausubel et al., *Current Protocols in Molecular Biology*, John Wiley & Sons, New York, N.Y. (1989), which are hereby incorporated by reference in their entirety.

Once the nucleic acid construct has been prepared, it is ready to be incorporated into a host cell. Basically, this method is carried out by transforming a host cell with the expression system of the present invention under conditions effective to yield transcription of the nucleic acid molecule in the host cell, using standard cloning procedures known in the art, such as described by Sambrook et al., *Molecular Cloning: A Laboratory Manual,* 2nd Edition, Cold Spring Harbor, N.Y., Cold Spring Harbor Laboratory Press, (1989), which is hereby incorporated by reference in its entirety. Suitable host cells include, but are not limited to, bacterial cells, fungal cells, viral cells, yeast cells, mammalian cells, insect cells, algal cells, plant cells, and the like. Methods of transformation may result in transient or stable expression of the DNA under control of the promoter.

Another embodiment relates to a method of making a transgenic plant having enhanced virus resistance compared to that of a non-transgenic plant. Generally, this method involves transforming a non-transgenic plant cell with a nucleic acid molecule according to the present invention under conditions effective to yield a transgenic plant cell having enhanced virus resistance compared to that of a non-transgenic plant. The transformed plant cell is then regenerated into a transgenic plant. Thus, as mentioned, supra, in other embodiments, the present invention includes transgenic plants and seeds produced by transformation with the nucleic acid molecule of the present invention.

Further aspects of the method of making the transgenic plant of the present invention are described below.

In one embodiment, the isolated nucleic acid of the present invention is stably inserted into the genome of the recombinant plant cell as a result of the transformation, although transient expression can serve an important purpose, particularly when the plant under investigation is slow-growing. Plant tissue suitable for transformation include leaf tissue, root tissue, meristems, zygotic and somatic embryos, callus, protoplasts, tassels, pollen, embryos, anthers, and the like.

The means of transformation chosen is that most suited to the tissue to be transformed. An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign DNA into plant cells. Another approach to transforming plant cells involves particle bombardment (also known as biolistic transformation) of the host cell, as disclosed in U.S. Pat. Nos. 4,945,050, 5,036,006, and 5,100,792, all issued to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety. Yet another method of introduction is fusion of protoplasts with other entities, either minicells, cells, lysosomes or other fusible lipid-surfaced bodies (Fraley et al., *Proc. Natl. Acad. Sci. USA* 79:1859-63 (1982), which is hereby incorporated by reference in its entirety). The DNA molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures*, Vol. 1, MacMillan Publishing Co., NY (1983); and Vasil (ed.), *Cell Culture and Somatic Cell Genetics of Plants*, Acad. Press, Orlando, Vol. I, 1984, and Vol. III (1986), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxins and cytokinins Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea, is useful, or the dhfr gene, which confers resistance to methotrexate (Bourouis et al., "Vectors Containing a Prokaryotic Dihydrofolate Reductase Gene Transform *Drosophila* Cells to Methotrexate-resistance," *EMBO J.* 2:1099-1104 (1983), which is hereby incorporated by reference in its entirety). Similarly, "reporter genes," which encode for enzymes providing for production of an identifiable compound, are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene by Southern blot hybridization analysis, using a probe specific to the transgenes contained in the given cassette used for transformation (Sambrook et al., *Molecular Cloning: A Laboratory Manual*, Cold Spring Harbor, N.Y., Cold Spring Harbor Laboratory Press (1989), which is hereby incorporated by reference in its entirety).

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the nucleic acid construct is present in the resulting plants. Alternatively, transgenic seeds or propagules (e.g., cuttings) are recovered from the transgenic plants. These seeds can then be planted in the soil and cultivated using conventional procedures to produce transgenic plants.

The methods and isolated nucleic acid molecules of the present invention can be used to impart virus resistance to plants against all types of plant viruses. In one embodiment, present invention is effective in imparting virus resistance to plants against viruses of the Potyviridae family. In particular, the methods and isolated nucleic acid molecules can be effective in imparting virus resistance to plants against Potyviridae viruses such as, without limitation, Lettuce Mosaic Virus ("LMV"), Pepper Mottle Virus ("PepMoV"), Potato Virus Y ("PVY"), Tobacco Etch Virus ("TEV"), and Turnip Mosaic Virus ("TuMV"). In one embodiment, the present invention can be used to impart virus resistance to plants against Potato Virus Y.

Examples of suitable plants, plant seeds, and/or plant cells that can be used in making or providing the transgenic plants, transgenic plant cells, and/or transgenic plant seeds of the present invention can include, without limitation, potato, rice, wheat, barley, rye, cotton, sunflower, peanut, corn, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, banana. In one embodiment the suitable plant that can be used in making or providing the transgenic plants, transgenic plant cells, and/or transgenic plant parts of the present invention is potato.

EXAMPLES

Example 1

Plant Materials Used

All plant material used in this study consists of potato cultivar 'Russet Burbank' clone 'Ida'. Multiple-node plants were obtained in culture from the North Dakota State Seed Department. The original plants were screened visually to ensure that plants appeared healthy. Cuttings were made from these healthy original plants and maintained on CM media (Table 1) with subculturing approximately every 60 days.

TABLE 1

Tissue culture media used during the course of this study.

| Media Name | Salts | Sucrose | Growth Regulators | Antibiotics | Vitamins | Agar | pH |
|---|---|---|---|---|---|---|---|
| CM | MS | 2% | None | None | PV | 8% | 5.7 |
| CIM | MS | 3% | BAP (1 mg/L) *NAA (1 mg/L) | None | MSVI, JHMS, 0.1% m-I | 6% | 5.6 |
| 3C5ZR+ | MS | 3% | IAA (0.5 mg/L) *Zeatin riboside (3 mg/L) | Timentin (300 mg/L) Kanamycin monosulfate (50 mg/L) | 3R, 0.1% m-I | 8% | 5.9 |
| MS | MS | 3% | None | None | MSVI, JHMS, 0.1% m-I | None | 5.6 |

*Components added after autoclaving

PV vitamins: 10% myo-inositol, 0.04% Thiamine HCL. Add 1 mL per liter of total media.

MSVI vitamins: 0.2% Glycine, 0.05% Nicotinic Acid, 0.05% Pyridoxine HCL, 0.04% Thiamine HCL. Add 1 mL per liter of total media.

JHMS vitamins: 0.025% Folic Acid. 0.005% d-biotin. Add 1 mL per liter of total media.

3R vitamins: 0.1% Thiamine HCL, 0.05% Nicotinic Acid, 0.05% Pyridoxine HCL. Add 1 mL per liter of total media.

m-I: myo-Inositol

Example 2

Sequencing of Potato eIF4E

RNA from leaves of potato cultivar 'Russet Burbank' clone 'Ida' was extracted using an RNeasy Plant Mini Kit (Qiagen Inc., Valencia, Calif., USA). Reverse transcriptase PCR was performed by incubating the resulting RNA with eIF4E Sac1R primer (Table 2), nucleotides, 5×MMLV buffer, RNase inhibitor, and RTase (Promega Corporation, Madison, Wis., USA) for 1 hour at 42 degrees. The resulting cDNA was then amplified by standard PCR using eIF4E Sma1 F and eIF4E Sac1 R primers (Table 2) (amplification cycle of 94 degrees for 45 seconds, 60 degrees for 45 seconds, 72 degrees for 45 seconds). The PCR product was run out on a 1% agarose gel. The single resulting band was cut, purified, ligated into the pCR 2.1-TOPO cloning vector (Invitrogen Corp., San Diego, Calif., USA), transformed into the accompanying TOP10 competent *E. coli*, and grown overnight. The following day, colony PCR was run on 18 separate colonies using M13 primers and the PCR product was sequenced in both the forward and reverse direction on an Automated 3730 DNA Analyzer (Applied Biosystems, Foster City, Calif., USA). Sequences were examined using Seqman software (DNASTAR Inc., Madison, Wis., USA).

TABLE 2

The major primers used during the course of this study.

| Primer Name | Primer Sequence | Application |
|---|---|---|
| eIF4E Sma1 F | TCCCCCGGGATGGCA ACAGCTGAAATGG (SEQ ID NO: 7) | Cloning into plant transformation vector pBI121 |
| eIF4E Sac1 R | TCCGAGCTCCTATAC GGTGTAACG (SEQ ID NO: 8) | Cloning into plant transformation vector pBI121 |

TABLE 2-continued

The major primers used during the course of this study.

| Primer Name | Primer Sequence | Application |
|---|---|---|
| eIF4E EcoRI F | CCGAATTCATGGCAA CAGCTGA (SEQ ID NO: 9) | Cloning into Y-2-H vector pJG4-5 |
| eIf4E XhoI R | TCCCTCGAGCTATAC GGTGTAACG (SEQ ID NO: 10) | Cloning into Y-2-H vector pJG4-5 |
| PVY VPg EcoRI F | TCCGAATTCATGAAA AATAAATCCAAAAG (SEQ ID NO: 11) | Cloning into Y-2-H vector pEG202 |
| PVY VPg Xho1 R | TCCCTCGAGCTAATGCT CCACTTCCTGTTTTGG (SEQ ID NO: 12) | Cloning into Y-2-H vector pEG202 |
| 35S F | GCTCCTACAAATGCC ATCATTGCG (SEQ ID NO: 13) | Confirming that shoots are transgenic |

Restriction sites are underlined and all primers are listed in the 5' to 3' orientation.

Example 3

Generation of Novel Alleles

Nucleotide polymorphisms were introduced by subjecting potato eIF4E, which was cloned into the pCR 2.1-TOPO cloning vector, to site-directed mutagenesis. This was performed using either the Quickchange Site-Directed Mutagenesis Kit or the Quickchange Multi Site-directed Mutagenesis Kit (both from Stratagene Corp, La Jolla, Calif., USA) following the manufacturer's directions. Primers were designed to introduce amino acid mutations to produce novel potato alleles with polymorphisms similar to those found in resistance alleles in other species. PVY strain O isolate Oz was obtained from Dr. K. Perry (Cornell University, Ithaca, N.Y.) and PVY strain NTN isolate PB312 was obtained from Dr. S. Gray (Cornell University and USDA-ARS, Ithaca, N.Y.). Both isolates were originally collected from infected potato fields in the State of New York.

Example 4

Yeast Two-Hybrid

Yeast two-hybrid was performed as previously described (Kang et al., "The pvr1 Locus in *Capsicum* Encodes a Translation Initiation Factor eIF4E that Interacts with Tobacco Etch Virus VPg," *Plant J* 42:392-405 (2005), which is hereby incorporated by reference in its entirety). Yeast strains and plasmid vectors were provided by Dr. G. B. Martin (Boyce Thompson Institute, Ithaca, N.Y.). Briefly, the bait plasmid pEG202 was used for the fusion of VPg from PVY strains O and NTN with the lexA DNA binding domain. The prey plasmid pJG4-5 was used to express potato eIF4E wildtype as well as several novel alleles generated by site-directed mutagenesis. The four primers used to introduce the proper restriction sites to eIF4E and VPg are shown in Table 2. Empty vectors and vectors containing resistant and susceptible pepper eIF4E were used as controls. Both of these plasmids were co-transformed into the yeast strain EGY48 containing the lacZ reporter plasmid pSH18-34. Colonies were tested for the presence of both pEG202 and pJG4-5 using colony PCR. Liquid cultures grown from these colonies were used for Western blot analysis with an anti-HA antibody to show expression of eIF4E. Protein extraction was performed according to (Kushnirov V., "Rapid and Reliable Protein Extraction From Yeast," *Yeast* 16:857-60 (2000), which is hereby incorporated by reference in its entirety) and immunoblot assay followed a previously described procedure (Printen et al., "Protein-protein Interactions in the Yeast Pheromone Response Pathway: Ste5p Interacts with All Members of the MAP Kinase Cascade," *Genetics* 138:609-19 (1994), which is hereby incorporated by reference in its entirety).

Example 5

Transformation of Potato

Potato eIF4E wildtype and mutant forms were cloned into the plant transformation vector pBI121 using the Sma1 and Sac1 restriction sites introduced by the eIF4E Sma1 F and eIF4E Sac1 R primers (Table 2). Proper ligation was verified by sequencing and vectors were transformed into *Agrobacterium tumefaciens*. Four kanamycin-resistant colonies were used to initiate a liquid culture that was incubated at 30 degrees C. overnight in 50 mL YM media (Yeast extract, 0.4 g/L; Mannitol, 10 g/L; NaCl, 0.1 g/L; Magnesium sulfate, 0.2 g/L; Monopotassium phosphate, 0.5 g/L) with 50 mg/L kanamycin monosulfate and 50 mg/L streptomycin. This culture was grown until the $OD_{600}$ reading was between 0.6 and 0.8. Cultures were centrifuged at 8000 rpm for 10 minutes and resuspended in 50 mL MS medium (Table 1). Roughly 200 stem internode explants per construct were incubated in this inoculum for 10 minutes and then plated on CIM medium. Co-cultivation occurred in the dark for 48 hours at 19 degrees C. Explants were then transferred to 3C5ZR medium weekly for 3 transfers, and then biweekly until a sufficient number of regenerated shoots were obtained. After approximately 8 weeks, regenerated shoots were excised and transferred to CM medium for rooting. Following 2 to 4 weeks of growth, DNA extraction was performed on leaf tissue following previously described methods (Edwards et al., "A Simple and Rapid Method for the Preparation of Plant Genomic DNA for PCR Analysis," *Nucleic Acids Res* 19:1349 (1991), which is hereby incorporated by reference in its entirety), and PCR was performed using 35S F primer and eIF4E Sac1 R primer (Table 2) (amplification cycle of 94 degrees for 45 seconds, 60 degrees for 45 seconds, 72 degrees for 45 seconds). PCR products were run out on a 1% agarose gel.

Example 6

Screening Transgenic Plants for Virus Resistance

Infected *Nicotiana tabacum* 'Samsun NN' leaves were taken from −20 degree C. storage, thawed, and macerated in phosphate-buffered saline (PBS consists of 3.2 mM $Na_2HPO_4$, 0.5 mM $KH_2PO_4$, 1.3 mM KCl, 135 mM NaCl, pH 7.4) with 0.05% Tween. Carborundum powder was sprinkled on young uninfected tobacco plants in the greenhouse and this solution was spread on 4 leaves per plant using 3 cotton swabs. Three weeks after infection, fresh inoculum was prepared from these infected tobacco plants by putting leaves through a leaf squeezer and diluting with PBS+0.05% Tween. Young potato plants were inoculated as described above for tobacco. Three weeks after infection, leaves were harvested and tested for virus susceptibility by double-antibody sandwich enzyme-linked immunosorbent assay (DAS-ELISA) as previously described (Baldauf et al., "Biological and Serological Properties of Potato Virus Y Isolates in Northeastern United States Potato," *Plant Disease* 90:559-566 (2006), which is hereby incorporated by reference in its entirety) using commercial antibody IFS to detect PVY strain NTN (Agdia Inc., Elkhart, Ind., USA). Equal amounts of fresh leaf tissue were sampled from multiple locations on the plants and used in ELISA detection the same day it was harvested. When possible, 4 plants per transformation event were tested. All plants with absorbance values significantly greater than uninoculated controls were considered susceptible.

Example 7

Potato eIF4E is Similar to its Tomato and Pepper Orthologs

The potato eIF4E gene was sequenced and found to be similar to orthologs from other cultivated species in the Solanaceae. Eighteen separate cDNA molecules of eIF4E were sequenced. Potato eIF4E cDNA is 696 nucleotides long and contains 231 amino acids plus a stop codon. Three similar but unique alleles of endogenous potato eIF4E were discovered (FIG. 1). Allele 1 was chosen arbitrarily and used for manipulation to generate novel, potentially resistant, potato eIF4E alleles. Relative to Allele 1, only 1 nonsynonymous nucleotide polymorphism exists in Allele 2, and only 3 nonsynonymous polymorphisms in Allele 3. None of the amino acid polymorphisms between the potato alleles are at sites known to be involved in virus resistance. Relative to Allele 1, there are two synonymous nucleotide polymorphisms in Allele 2, and 8 synonymous nucleotide polymorphisms in Allele 3. Allele 2 appears to be a recombinant allele of Allele 1 and Allele 3 with the recombination breakpoint occurring somewhere between nucleotides 279 and 413 (FIG. 1).

Figure 2:
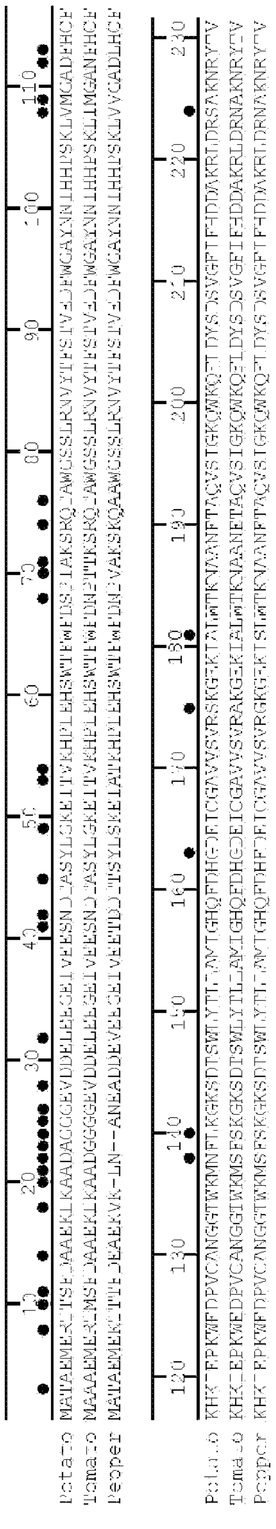
FIG. 2 is the amino acid alignment of eIF4E orthologs from potato (from *Solanum tuberosum* cultivar 'Russet Burbank' clone 'Ida') (SEQ ID NO: 1), tomato (from *Solanum lycopersicum*) (NCBI Accession No. AAV88611) (SEQ ID NO: 5), and pepper (from *Capsicum annuum* 'Jupiter') (SEQ ID NO: 6) Solid circles identify amino acid polymorphisms between species.

Potato eIF4E is very similar to the tomato ortholog pot-1 and the pepper ortholog pvr1 (FIG. 2) (Kang et al., "The pvr1 Locus in *Capsicum* Encodes A Translation Initiation Factor eIF4E That Interacts with Tobacco Etch Virus VPg," *Plant J* 42:392-405 (2005); Ruffel et al., "A Natural Recessive Resistance Gene Against Potato Virus Y in Pepper Corresponds to the Eukaryotic Initiation Factor 4E (eIF4E)," *Plant J* 32:1067-75 (2002); Ruffel et al., "The Recessive Potyvirus Resistance Gene Pot-1 is the Tomato Orthologue of the Pepper pvr2-eIF4E Gene," *Mol Genet Genomics* 274:346-53 (2005), which are hereby incorporated by reference in their entirety). Potato Allele 1 shares 97% nucleotide identity and 95% amino acid identity with the susceptible tomato allele Pot-$1^+$. It is also similar to the pepper ortholog pvr1, sharing 88% nucleotide identity and 86% amino acid identity with the susceptible allele Pvr$1^+$. The first 19 and last 15 nucleotides of the alignment were not used for these calculations since these nucleotides in the potato sequence were dictated by the primers used in the initial amplification. Like tomato, potato eIF4E has 3 more amino acids than the pepper ortholog. The exact location of these insertions is not known with a high degree of certainty, but appears to occur between amino acids 19 and 29, a region that is not thought to influence virus resistance or susceptibility.

Example 8

Novel Potato Alleles were Generated by Site-Directed Mutagenesis

Five unique potato eIF4E alleles were generated by site-directed mutagenesis with the intent of generating a resistant allele in potato that may be expressed transgenically to engineer virus-resistant plants (Table 3). A good deal of information has been generated regarding the effect of specific amino acid polymorphisms, either singly or in combination with multiple amino acid changes, on the interaction of host eIF4E from solanaceous hosts with viral VPg (Charron et al., "Natural Variation and Functional Analyses Provide Evidence for Co-Evolution Between Plant eIF4E and Potyviral VPg," *Plant J* 54:56-68 (2008); Kang et al., "The pvr1 Locus in *Capsicum* Encodes a Translation Initiation Factor eIF4E that Interacts with Tobacco Etch Virus VPg," *Plant J*42:392-405 (2005); Ruffel et al., "A Natural Recessive Resistance Gene Against Potato Virus Y in Pepper Corresponds to the Eukaryotic Initiation Factor 4E (eIF4E)," *Plant J*32:1067-75 (2002); Ruffel et al., "The Recessive Potyvirus Resistance Gene Pot-1 is the Tomato Orthologue of the Pepper pvr2-eIF4E Gene," *Mol Genet Genomics* 274:346-53 (2005); Yeam et al., "Functional Dissection of Naturally Occurring Amino Acid Substitutions in eIF4E that Confers Recessive Potyvirus Resistance in Plants," *Plant Cell* 9:2913-2928 (2007), which are hereby incorporated by reference in their entirety). This information was used to induce polymorphisms in potato eIF4E with the intent of disrupting the eIF4E-VPg interaction. These novel potato alleles were transgenically expressed to develop virus-resistance in potato.

First, novel allele Potato4E:G110R was created by introducing mutation G110R. This mutation is similar to the G107R mutation generated in pepper eIF4E and conferring TEV resistance in transgenic tomato plants (Yeam et al., "Functional Dissection of Naturally Occurring Amino Acid Substitutions in eIF4E that Confers Recessive Potyvirus Resistance in Plants," *Plant Cell* 9:2913-2928 (2007), which is hereby incorporated by reference in its entirety). Second, novel allele Potato4E:pvr1+pvr$1^2$ was created by introducing mutations P69T, G110R, I70N, L82R, and D112N. This allele was generated to mimic all the nucleotide polymorphisms from pepper alleles pvr1 and pvr$1^2$ combined into a single allele. When this was performed on the pepper eIF4E, it conferred TEV resistance in transgenic tomato plants (Yeam et al., "Functional Dissection of Naturally Occurring Amino Acid Substitutions in eIF4E that Confers Recessive Potyvirus Resistance in Plants," *Plant Cell* 9:2913-2928 (2007), which is hereby incorporated by reference in its entirety). An amino acid mutation was not made at site V54 since valine is biochemically similar to alanine, the amino acid found at the homologous position in the resistant pepper allele. Third, novel allele Potato4E:pvr$1^2$ was created by introducing mutations I70N, L82R, and D112N in order to mimic the amino acid mutations in pepper resistance allele pvr$1^2$. Fourth, novel allele Potato4E: pvr$1^2$E was made containing mutations I70E, L82R, and D112N. This allele is similar to the previous allele but contains a positive charge at site 70. Finally, allele Potato4E:pot-1 was created by introducing mutations L48F, S68K, A77D, and M109I in order to mimic the amino acid mutations in tomato resistance allele pot-1.

Table 3

Novel potato eIF4E alleles. Description of the amino acid mutations introduced into potato eIF4E Allele 1 to generate potentially resistant novel alleles.

| Allele Name | Mutations introduced in wildtype Potato eIF4E |
|---|---|
| 1) Potato4E: G110R | G110R |

Table 3-continued

Novel potato eIF4E alleles. Description of the amino acid mutations introduced into potato eIF4E Allele 1 to generate potentially resistant novel alleles.

| Allele Name | Mutations introduced in wildtype Potato eIF4E | | | | |
|---|---|---|---|---|---|
| 2) Potato4E: pvr1 + pvr1$^2$ | P69T | G110R | I70N | L82R | D112N |
| 3) Potato4E: pvr1$^2$ | | | I70N | L82R | D112N |
| 4) Potato4E: pvr1$^2$E | | | I70E | L82R | D112N |
| 5) Potato4E: pot-1 | L48F | S68K | A77D | M109I | |

Example 9

All Novel Potato Alleles Tested Disrupt the eIF4E-VPg Interaction

Figure 3:
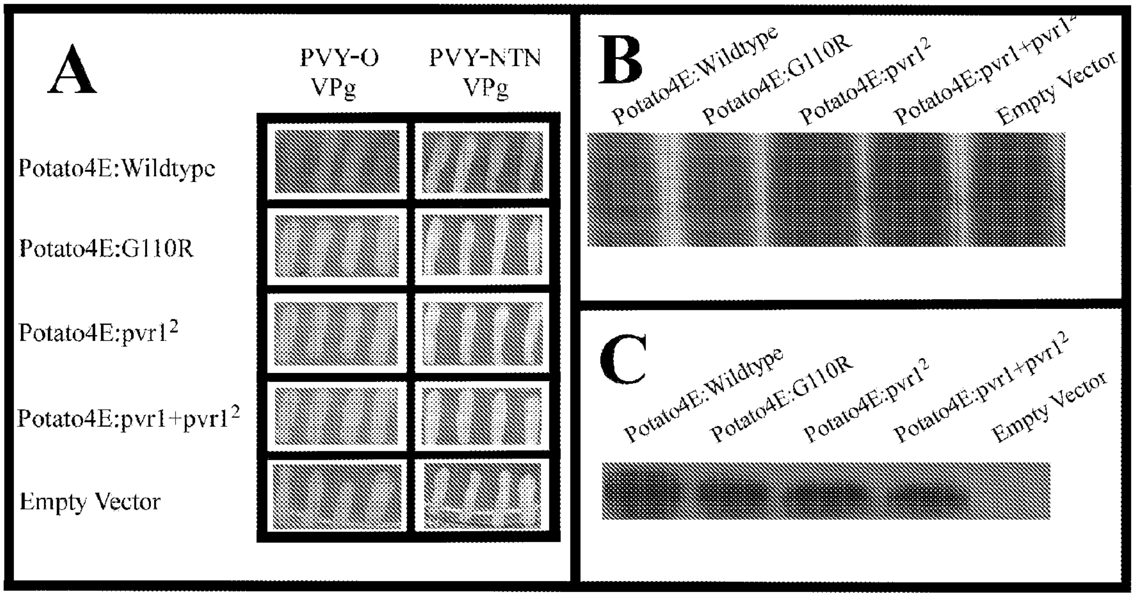
FIGS. 3A-C show the results obtained from yeast two-hybrid experiments.

Three of the 5 novel potato eIF4E proteins generated in this study were assayed using yeast two-hybrid analysis to examine whether the introduced amino acid changes resulted in the desired disruption of the interaction with the viral VPg protein. In all alleles tested, this interaction appears to be disrupted (FIG. 3A-C). A strong blue color developed when wildtype eIF4E was tested with the VPg protein from both strains of Potato virus Y (PVY) tested. In contrast, yeast colonies containing an empty vector control remained white. Three alleles were tested: Potato4E:G110R, Potato4E:pvr1$^2$, and Potato4E:pvr1+pvr1$^2$. No interaction was observed between any of these 3 alleles and VPg from either PVY strain 0 or PVY strain N. The amino acid mutations introduced into the susceptible version of potato eIF4E appear to prevent PVY VPg from binding potato eIF4E.

Example 10

Figure 4:
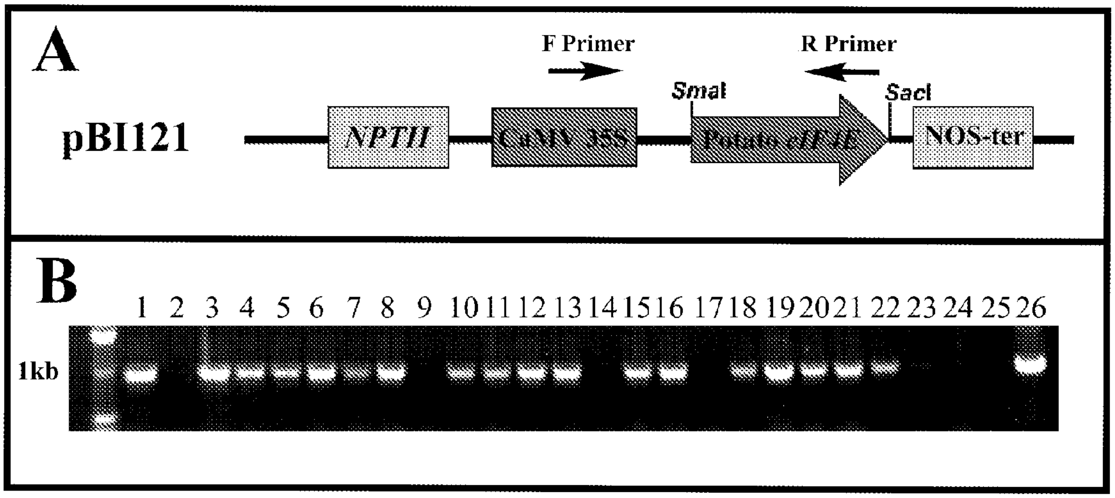
FIGS. 4A-B depict the location of primers used to identify transgenic potato shoots (FIG. 4A) and results of PCR (FIG. 4B).
Figure 5:
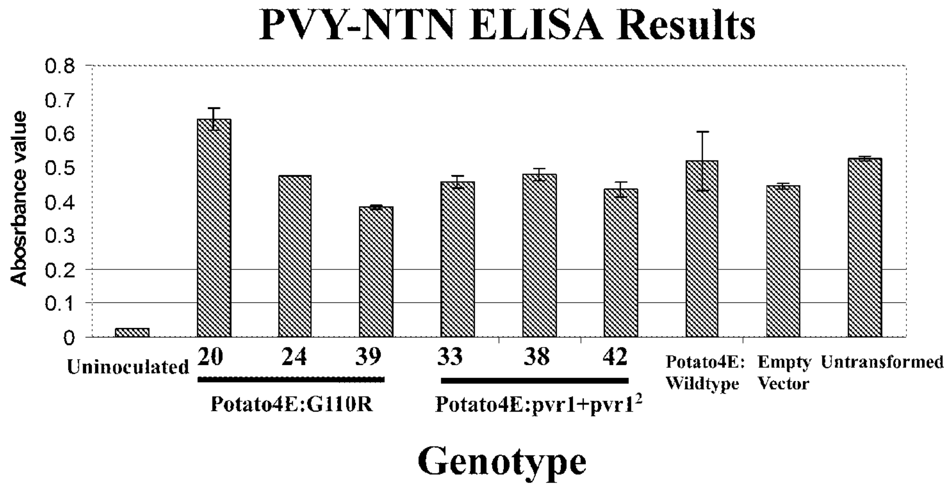
FIG. 5 shows the ELISA results for Potato4E:G110R and Potato4E:pvr1+pvr1$^2$. Three separate transgenic events for each construct plus appropriate controls are shown. Two regenerants per construct were challenged with PVY-NTN. ELISA results indicate no difference between experimental lines and positive controls.

Intragenic' Expression of the Potato4E:pvr12 Allele Results in Virus Resistant Plants All five of the novel potato eIF4E alleles were ligated into the pBI121 plant transformation vector containing the constitutive promoter CaMV 35S and kanamycin resistance gene NPTII selectable marker. These constructs were used in *Agrobacterium*-mediated plant transformation of potato stem internode explants. Regenerating shoots were excised, rooted, and screened using polymerase chain reaction to confirm that they were transgenic (FIG. 4A-B). Regeneration efficiency of the three constructs that have been tested at this stage are shown (Table 4). Transgenic plants were then transferred to soil, multiplied by clonal propagation of stem cuttings, and challenged with PVY strain NTN. Three weeks post inoculation, leaf samples were collected and ELISA was performed. The concentration of viral coat protein was measured using a spectrophotometer. Results for the two alleles Potato4E:G110R and Potato4E:pvr1+pvr1$^2$ are shown in FIG. 5. For both of these alleles virus coat protein developed to levels comparable to the positive controls, indicating that they do not function to confer virus resistance when overexpressed in potato despite the fact that the eIF4E interaction appeared to be disrupted as measured by yeast two-hybrid analysis.

Figure 6:
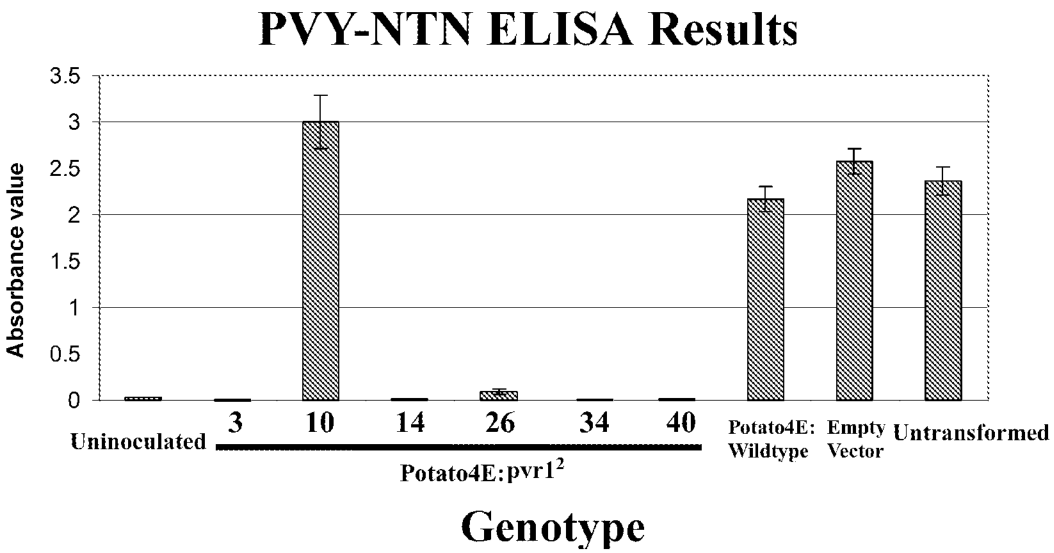
FIG. 6 shows ELISA results for Potato4E:pvr1$^2$. Six separate transgenic events are shown. Four regenerants per construct were challenged with PVY NTN. ELISA results indicate a significant difference between several experimental lines and positive controls.

Results for the allele Potato4E:pvr1$^2$ are quite different. The absorbance values of the potato plants expressing this novel allele were comparable to the untransformed negative controls and significantly less than the positive controls (FIG. 6). A minority of transgenic lines, such as event 10 in FIG. 6, however, remained virus susceptible despite the fact that they contain the transgene. Thus, when this modified potato eIF4E allele, which was subjected to 3 amino acid changes relative to wildtype, was expressed transgenically, many of the regenerant potato plants were resistant to PVY strain NTN. The percentage of separate transformation events that are virus resistant are shown in Table 4.

The virus resistance phenotypes of novel potato alleles Potato4E:pvr1$^2$E and Potato4E:pot-1 were determined. This data is also shown in the Table 4. Results obtained thus far show relatively constant regeneration efficiency across constructs. Allele Potato4E:pvr1$^2$ has yielded a high percentage of resistant lines. The other lines tested thus far have not.

Table 4

Transformation results broken down by construct.

| Allele used in transformation procedure | # explants transformed | # regenerant plants tested | Regeneration efficiency | # resistant lines obtained | % resistant lines |
|---|---|---|---|---|---|
| Potato4E: G110R | 112 | 17 | 15.2% | 0 | 0% |
| Potato4E: pvr1 + pvr1$^2$ | 207 | 27 | 13.0% | 0 | 0% |
| Potato4E: pvr1$^2$ | 184 | 30 | 16.3% | 25 | 83% |
| Potato4E: pvr1$^2$E | 202 | 10 | 5.0% | 6 | 60% |
| Potato4E: pot-1 | 235 | 12 | 5.1% | 0 | 0% |

Example 11

Testing of Resistance Allele Potato4E:pyr12

Figure 7:
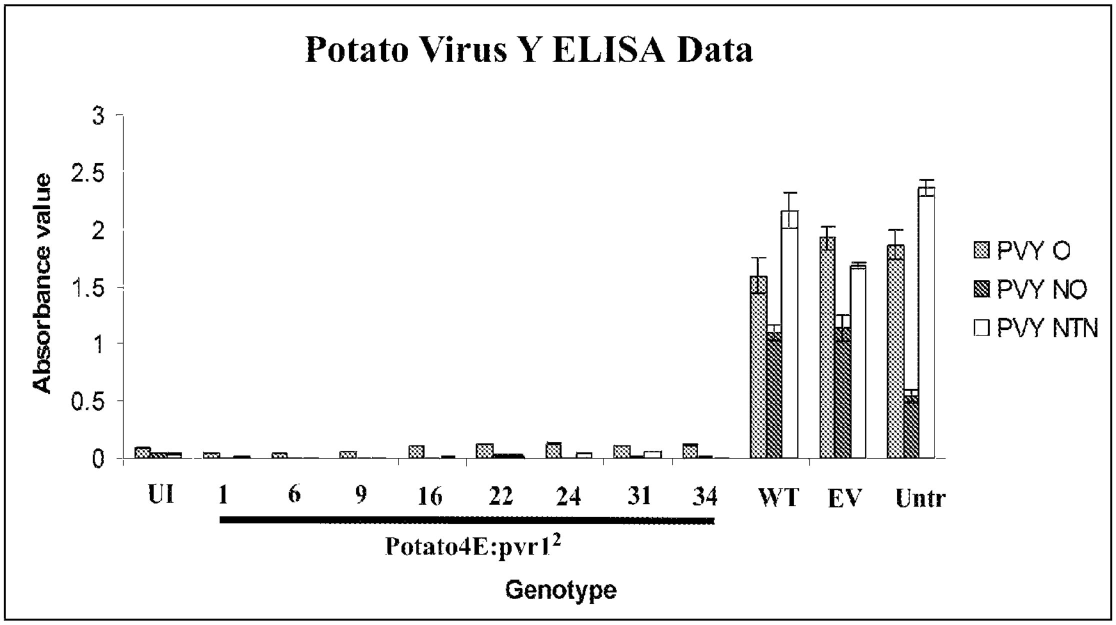
FIG. 7 shows ELISA results for Potato4E: pvr1$^2$. Eight separate transgenic lines are shown. Four individuals per line were challenged with either PVY strain NTN, NO, and O. ELISA results indicate the 8 lines tested had significantly less virus accumulation than the susceptible controls. In this figure, UI represents uninoculated, transgenic plants expressing wildtype potato eIF4E allele 1 are represented by WT, empty vector control (expresses GUS gene) is shown as EV, and nontransgenic potato cultivar 'Russet Burbank' that was regenerated from tissue culture is shown as NT.

Eight transgenic lines of this allele that were observed to be resistant to PVY strain NTN were further tested using two additional strains, NO and O. In all cases, the plants that were immune to strain NTN were immune to the other strains as well (FIG. 7).

Example 12

Virus Inoculation

Figure 8:
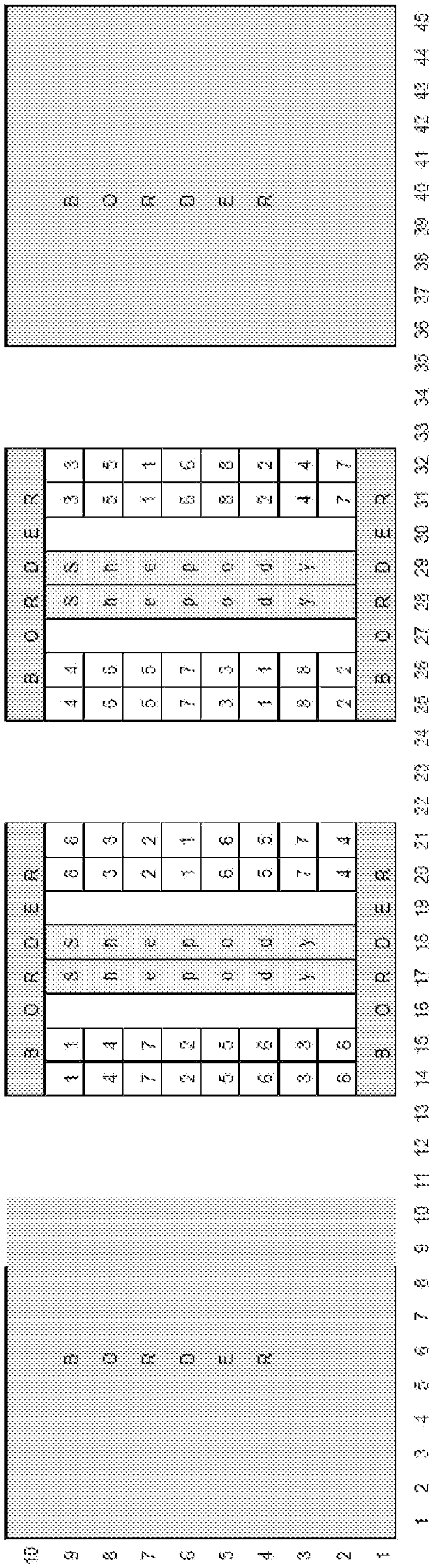
FIG. 8 shows a schematic of field planting plan of transgenic potato plants in Ithaca, N.Y. A 30' border surrounding the plot was necessary to satisfy USDA-APHIS requirements for release of transgenic material (notification number 08-329-102n). Yellow-shaded Shepody rows were virus inoculated with a mixture of Potato virus Y (PYV) strains NTN, NO, and O. Genotypes 1-8 consist of experimental lines, 4 of which (numbers 2, 6, 7, and 8) are putatively resistant transgenic plants expressing allele Potato4E:pvr1$^2$. Genotype 1 is a nontransgenic potato cultivar. Genotype 3 is a transgenic plant expressing the unmodified potato eIF4E allele. Genotype 4 is a transgenic plant expressing the GUS gene. Genotype 5 is a transgenic potato expressing the pepper resistance gene pvr1$^2$. Each square represents 24 plants at 10.6 inch in-row spacing. Spacing between rows was 3 feet.

Potato virus Y strains NTN, NO, and O were inoculated using mechanical inoculation. For field inoculations, 4 rows of potato cultivar 'Shepody' (shaded yellow in FIG. 8) were inoculated using an air compressor and a paint sprayer that sprayed a combination of viral inoculum (made from putting infected *Nicotiana tobaccum* leaves through a leafsqueezer with PBS buffer+tween) and carborundum. Experimental lines were not inoculated directly, but relied on aphid populations for infection.

Example 13

Field Planting

Field locations in Ithaca, N.Y. and Kimberly, Id. were planted with transgenic tubers representing 4 putatively virus resistant transgenic potato lines expressing the mutated eIF4E allele Potato4E:pvr1$^2$. Also included was a potato transgenically expressing the pepper resistance gene pvr1$^2$, a potato plant expressing the unmodified version of potato eIF4E, a potato plant expressing the GUS gene, and a potato plant that was not genetically modified (FIG. 8). 4 replicates per site were included. Each replicate had either 1 (Idaho) or 2 (Ithaca) 24 plant rows with 10.6 inch in-row spacing and 3 feet between rows. Experimental lines (numbered 1 through 8) were separated by the virus-susceptible cultivar 'Shepody', which was mechanically inoculated with virus. Virus was moved from inoculated lines to experimental lines by natural aphid populations as well as aphids that were reared and released on site. Leaf samples were collected at first emergence and at the end of the growing season and analyzed using ELISA. Eight 5-leaf bulk samples were analyzed per line per replicate.

Example 14

Field Results

The three susceptible check lines all contained a high percentage of virus positive samples. All samples for the 4 lines expressing allele Potato4E:pvr$1^2$, however, were all virus negative (Table 5). Eight 5-leaf bulks were taken per line per replicate. Genotypes 2, 6, 7, and 8 are putatively resistant transgenic plants expressing allele Potato4E:pvr$1^2$. Genotype 1 is a nontransgenic potato cultivar. Genotype 3 is a transgenic plant expressing the unmodified potato eIF4E allele. Genotype 4 is a transgenic plant expressing the GUS gene. Genotype 5 is a transgenic potato expressing the pepper resistance gene pvr$1^2$. Thus, under high disease pressure, the virus resistance generated using the methods of the present invention appears to be effective when the plants are grown under agricultural conditions.

TABLE 5

Number of PVY positive samples from field sampling.

| | Number of PVY Positive Samples | | | | |
|---|---|---|---|---|---|
| Genotype | Replicate I | Replicate II | Replicate III | Replicate IV | Total |
| 1 | 6/8 | 8/8 | 8/8 | 8/8 | 30/32 |
| 2 | 0/8 | 0/8 | 0/8 | 0/8 | 0/32 |
| 3 | 8/8 | 6/8 | 7/8 | 8/8 | 29/32 |
| 4 | 5/8 | 8/8 | 8/8 | 6/8 | 27/32 |
| 5 | 0/8 | 0/8 | 0/8 | 0/8 | 0/32 |
| 6 | 0/8 | 0/8 | 0/8 | 0/8 | 0/32 |
| 7 | 0/8 | 0/8 | 0/8 | 0/8 | 0/32 |
| 8 | 0/8 | 0/8 | 0/8 | 0/8 | 0/32 |

Example 15

Potato eIF4E is Similar to the Tomato Ortholog Pot-1 and the Pepper Ortholog pvr1 eIF4E from a number of plant species have been described including *Arabidopsis* (Yoshii et al., "The *Arabidopsis* Cucumovirus Multiplication 1 and 2 Loci Encode Translation Initiation Factors 4E and 4G," *J Virol* 78:6102-11 (2004), which is hereby incorporated by reference in its entirety), barley (Stein et al., "The Eukaryotic Translation Initiation Factor 4E Confers Multiallelic Recessive Bymovirus Resistance in *Hordeum Vulgare* (L.)," *Plant J* 42:912-22 (2005), which is hereby incorporated by reference in its entirety), corn (Manjunath et al., "Oxygen Deprivation Stimulates $Ca^{2+}$-Mediated Phosphorylation of mRNA Cap-Binding Protein eIF4E in Maize Roots," *The Plant Journal* 19:21-30 (1999), which is hereby incorporated by reference in its entirety), melon (Nieto et al., "An eIF4E Allele Confers Resistance to an Uncapped and Non-Polyadenylated RNA Virus in Melon," *Plant J* 48:452-62 (2006), which is hereby incorporated by reference in its entirety), pepper (Kang et al., "The pvr1 Locus in *Capsicum* Encodes a Translation Initiation Factor eIF4E that Interacts with Tobacco Etch Virus VPg," *Plant J* 42:392-405 (2005); Ruffel et al., "A Natural Recessive Resistance Gene Against Potato Virus Y in Pepper Corresponds to the Eukaryotic Initiation Factor 4E (eIF4E)," *Plant J* 32:1067-75 (2002), which are hereby incorporated by reference in their entirety), lettuce (Nicaise et al., "The Eukaryotic Translation Initiation Factor 4E Controls Lettuce Susceptibility to the Potyvirus Lettuce Mosaic Virus," *Plant Physiol* 132:1272-82 (2003), which is hereby incorporated by reference in its entirety), pea (Gao et al., "The Potyvirus Recessive Resistance Gene, sbm1, Identifies a Novel Role for Translation Initiation Factor eIF4E in Cell-To-Cell Trafficking," *The Plant Journal* 40:376-385 (2004), which is hereby incorporated by reference in its entirety), tomato (Ruffel et al., "The Recessive Potyvirus Resistance Gene Pot-1 is the Tomato Orthologue of the Pepper pvr2-eIF4E Gene," *Mol Genet Genomics* 274:346-53 (2005), which is hereby incorporated by reference in its entirety), and wheat (Monzingo et al., "The Structure of Translation Initiation Factor eIF4E from Wheat Reveals a Novel Disulfide Bond," *Plant Physiol* (2007), which is hereby incorporated by reference in its entirety). The present invention is the first to describe the eIF4E gene in potato. Polymerase chain reaction amplification of potato eIF4E yielded a single band. Sequencing of individual cDNA molecules resulted in the discovery of three similar alleles, one apparently a result of an intergenic recombination event between the other two. Although this gene appears to be from a multigene family (Browning K., "Plant Translation Initiation Factors: It is Not Easy to Be Green," *Biochem Soc Trans* 32:589-91 (2004); Robaglia et al., "Translation Initiation Factors: A Weak Link in Plant RNA Virus Infection," *Trends Plant Sci* 11:40-5 (2006), which are hereby incorporated by reference in their entirety), the high degree of similarity between these alleles suggests that the primers used resulted in amplification of a single gene copy. The high degree of similarity to the potato ortholog pot-1 and the pepper ortholog pvr1 strongly suggests that the gene isolated from potato in the present invention is the direct ortholog of both of these resistance genes. This was important to establish since PVY has been shown to utilize pot-1 and pvr1 specifically, and apparently not other members of the multi-gene family such as eIF$(iso)_4$E (Kang et al., "The pvr1 Locus in *Capsicum* Encodes a Translation Initiation Factor eIF4E that Interacts with Tobacco Etch Virus VPg," *Plant J* 42:392-405 (2005); Ruffel et al., "A Natural Recessive Resistance Gene Against Potato Virus Y in Pepper Corresponds to the Eukaryotic Initiation Factor 4E (eIF4E)," *Plant J* 32:1067-75 (2002); Ruffel et al., "The Recessive Potyvirus Resistance Gene Pot-1 is the Tomato Orthologue of the Pepper pvr2-eIF4E Gene," *Mol Genet Genomics* 274:346-53 (2005), which are hereby incorporate by reference in their entirety).

Example 16

Novel Potato eIF4E Alleles have been Constructed that Disrupt the Interaction with VPg The high degree of similarity of the potato gene to homologous virus resistance genes in other related plant species made it possible to confidently align the potato sequence with that of tomato and pepper. Differences between susceptible and resistant forms of pot-1 and pvr1 from these species provided predictions of which amino acids in the potato eIF4E protein are involved in the interaction with the viral protein VPg. Interuption of the eIF4E-VPg interaction has proven to be a necessary feature of resistant versions of eIF4E, as indicated by yeast two-hybrid assay (Kang et al., "The pvr1 Locus in *Capsicum* Encodes a Translation Initiation Factor eIF4E that Interacts with Tobacco Etch Virus VPg," *Plant J* 42:392-405 (2005), which is hereby incorporated by reference in its entirety) and bimolecular fluorescence complementation (Yeam et al., "Functional Dissection of Naturally Occurring Amino Acid Substitutions in eIF4E that Confers Recessive Potyvirus Resistance in Plants," *Plant Cell* 9:2913-2928 (2007), which is hereby incorporated by reference in its entirety). Although no natural resistance alleles at this locus in potato are known, it is hypothesized that they could be constructed in the laboratory and expressed transgenically to confer resistance in potato. Of the 5 different novel alleles that were made by mutating the susceptible wildtype version, 3 have been tested for interruption of the VPg interaction via yeast two-hybrid analysis. The fact that all 3 alleles, even one with a single amino acid change relative to wildtype, is enough to break this interaction underscores how small mutations can have large phenotypic consequences. This factor is likely responsible for the evolution of disease resistance at this locus repeatedly in so many unrelated plant taxa.

Example 17

Successful Development of Resistant Plants with Potentially Improved Consumer Acceptance Novel potato eIF4E alleles Potato4E:G110R, which has a single amino acid mutation, and Potato4E:pvr1+pvr1$^2$, which has 5 amino acid changes, did not confer virus resistance when expressed transgenically in potato plants. The plants were not virus resistant despite the fact that the interaction of eIF4E and VPg appeared to be disrupted in the yeast two-hybrid analysis. Interruption of the binding between these proteins is necessary for virus resistance; however, it does not appear to be sufficient. As noted in (Kang et al., "The pvr1 Locus in *Capsicum* Encodes a Translation Initiation Factor eIF4E that Interacts with Tobacco Etch Virus VPg," *Plant J* 42:392-405 (2005), which is hereby incorporated by reference in its entirety), pepper allele pvr1$^1$ did not interact with VPg but still became infected with two different strains of Tobacco Etch Virus (TEV). By introducing 1 mutation, it seems likely that the effect on the eIF4E protein is not dramatic enough to entirely exclude utilization by the virus.

The novel allele Potato4E:pvr1$^2$ contains 2 fewer amino acid changes than Potato4E:pvr1+pvr1$^2$ and successfully confers virus resistance when overexpressed in wild-type plants. Thus, making 5 amino acid changes did not result in virus resistance, but making 3 of those 5 did. It has been discovered that the reason having all 5 amino acid mutations does not provide virus resistance is that the eIF4E protein cannot tolerate so many mutations. Steric hindrance or other factors may make the protein unstable or it may fold improperly and be targeted for degradation. If this occurred, transgenic protein would not accumulate to appreciable levels and virus resistance would not be obtained. Thus, in order to obtain virus-resistant plants, enough amino acid mutations must be introduced such that the interaction with the virus is interrupted, but not so many mutations can be introduced that eIF4E's structural integrity is compromised. The present invention identifies mutations which provide virus resistance.

By generating virus-resistant plants using a gene from within the potato genome, a process categorized by a growing body of researchers as "intragenic", the market acceptance of virus-resistant potatoes may be improved (Nielsen K., "Transgenic Organisms—Time For Conceptual Diversification?," *Nat Biotechnol* 21:227-8 (2003); Rommens C., "Intragenic Crop Improvement: Combining the Benefits of Traditional Breeding and Genetic Engineering," *J Agric Food Chem* 55:4281-8 (2007); Rommens C., "The Need for Professional Guidelines in Plant Breeding," *Trends in Plant Science* 13:261-263 (2008), which are hereby incorporated by reference in their entirety). Previous attempts at genetic engineering in potatoes have relied upon pathogen derived resistance, whereby the viral coat protein is expressed in the potato plants, to obtain virus resistant plants. Concerns over the expression of viral genes was a contributing factor to the decision of major potato producers to cease sales of genetically engineered potato (Kaniewski et al., "The Potato Story," *AgBio Forum* 7:41-46 (2004), which is hereby incorporated by reference in its entirety). There is some evidence to suggest that consumers would look more favorably upon genetic engineering of vegetables that are transformed with genes from within sexually compatible germplasm sources (Lusk et al., "Consumer Acceptance of Genetically Modified Foods," *Food Technology* 56:32-37 (2002), which is hereby incorporated by reference in its entirety). By genetically engineering potato to be virus resistant using culturally acceptable methods, the present invention can be used to develop a useful plant variety with a maximized likelihood of commercialization.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A nucleic acid molecule encoding a mutant form of wild-type eIF4E, wherein the mutant form imparts Potyviridae virus resistance to potato and has a mutation with respect to the wild-type amino acid sequence of SEQ ID NO: 1, wherein the mutant form comprises: (1) mutations of I70N, L82R, and D112N with respect to SEQ ID NO: 1 or (2) mutations of I70E, L82R, and D112N with respect to SEQ ID NO: 1.

2. A nucleic acid construct comprising:

a promoter;

a termination sequence; and the nucleic acid molecule of claim 1 operatively connected to said promoter and said termination sequence.

3. An expression vector comprising the nucleic acid molecule of claim 1.

4. A cell comprising the nucleic acid molecule of claim 1.

5. The cell according to claim 4, wherein said cell is selected from the group consisting of a plant cell and a bacterial cell.

6. A transgenic plant comprising the nucleic acid molecule of claim 1.

7. The transgenic plant of claim 6, wherein the plant is selected from the group consisting of potato, rice, wheat, barley, rye, cotton, sunflower, peanut, corn, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and banana.

8. The transgenic plant of claim 7, wherein the plant is potato.

9. A transgenic plant seed comprising the nucleic acid molecule of claim 1.

10. The transgenic plant seed of claim 9, wherein the seed is from a plant selected from the group consisting of potato, rice, wheat, barley, rye, cotton, sunflower, peanut, corn, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and banana.

11. The transgenic plant seed of claim 10, wherein the plant is potato.

12. A method of imparting virus resistance to a plant, said method comprising:

providing a transgenic plant or a transgenic plant seed comprising the nucleic acid molecule of claim 1, and growing the transgenic plant or a plant produced from the transgenic plant seed under conditions effective to impart Potyviridae virus resistance to the plant.

13. The method of claim 12, wherein a transgenic plant is provided.

14. The method of claim 12, wherein a transgenic plant seed is provided.

15. The method of claim 12, wherein the plant is selected from the group consisting of potato, rice, wheat, barley, rye, cotton, sunflower, peanut, corn, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and banana.

16. The method of claim 15, wherein the plant is potato.

17. The method of claim 16, wherein the potato plant is resistant to Potyviridae viruses.

18. A method of imparting virus resistance to a plant, said method comprising:

providing the cell of claim 4, wherein the cell is a plant cell, and regenerating a plant from the plant cell, wherein the regenerated plant is resistant to Potyviridae viruses.

19. The method of claim 18, wherein the plant is selected from the group consisting of potato, rice, wheat, barley, rye, cotton, sunflower, peanut, corn, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and banana.

20. The nucleic acid molecule of claim 1, wherein the nucleic acid molecule is in the form of a cDNA sequence.

* * * * *